United States Patent [19]

Kotowski et al.

[11] Patent Number: 4,963,244
[45] Date of Patent: Oct. 16, 1990

[54] TEST CELL FOR IDENTIFYING DEACTIVATED SURFACE AREAS OF AN ELECTRODE

[75] Inventors: Stephan Kotowski, Seligenstadt; Bernd Busse, Darmstadt; Bernd Donnerhak, Maintal, all of Fed. Rep. of Germany

[73] Assignee: Heraeus Elektroden GmbH, Hanau am Main, Fed. Rep. of Germany

[21] Appl. No.: 468,540

[22] Filed: Jan. 23, 1990

Related U.S. Application Data

[62] Division of Ser. No. 403,671, Sep. 6, 1989, Pat. No. 4,919,766.

[30] Foreign Application Priority Data

Nov. 3, 1988 [DE] Fed. Rep. of Germany ....... 3837290

[51] Int. Cl.$^5$ .......................................... G01N 27/416
[52] U.S. Cl. ................................................... 204/400
[58] Field of Search ............................. 204/153.1, 400

[56] References Cited

U.S. PATENT DOCUMENTS 3,408,270 10/1968 Gentile ............................. 204/153.1
4,511,838 4/1985 Reichman et al. ................. 324/71.5

Primary Examiner—G. L. Kaplan
Attorney, Agent, or Firm—Felfe & Lynch

[57] ABSTRACT

Process for the visual inspection of an electrode (anode) having an activated layer for electrogalvanizing plants for steel bands in which the electrode to be tested is inserted between anode and cathode of a sodium sulfate electrolytic cell with the surface to be tested facing toward the cathode. After a voltage is applied the development of the gas bubbles on the activated layer is monitored by means of a video camera.

1 Claim, 2 Drawing Sheets

TEST CELL FOR IDENTIFYING DEACTIVATED SURFACE AREAS OF AN ELECTRODE

This is a division of Ser. No. 403,671 filed Sept. 6,1989 and now Pat. No. 4,919,766.

BACKGROUND OF THE INVENTION

The invention relates to a process for identifying deactivated surface areas of a basically flat electrode for electrochemical processes, especially an anode for electro-galvanizing plants for steel bands, and a device for the working of this process.

Titanium anodes coated with metal oxides of the platinum group are also used for electrogalvanizing steel bands which serve, for example, for the manufacture of galvanized automobile bodies. After a certain time the titanium anodes lose their activity and must be reactivated after removing. For this purpose the entire galvanizing plant must be shut down which temporarily paralyzes the entire production process. Hence, it is desirable to be able to assess during an intended standstill of the plant -which is in any way necessary due to different reasons- whether the anodes will last until the next intended standstill or whether they have to be immediately replaced for reasons of safety.

Presently, the following methods are used to assess if the anodes are still active or not:

(a) Measuring the thickness of the activated layer by means of X-ray fluorescent analysis (only possible during a standstill): This process is very time consuming and can hardly be applied for all anodes during a standstill Despite a high remaining layer thickness the anodes can be inactive due to passivity below the active layer. Measuring is only possible where the diameter does not exceed 5 cm. Many individual measurings must hence be carried out and evaluated in order to assess an entire area of 1 m², for example.

(b) Measuring the potential (only possible during standstill): This process, too, is very time consuming and does therefore not permit measuring all anodes during standstill. Again, only a point-by-point measuring is possible.

(c) Shutting down individual anodes during operation: This process permits a continuous measuring of the thickness of the layer of the coated zinc. If the layer is uneven, individual anodes are shut down. If this makes the coating more even these anodes are no more considered to be fit for operation. This process cannot be applied in every plant. The layers can also be uneven for reasons other then deactivated anodes.

(d) Galvanizing during standstill of the band: If the steel band which during regular operation travels through the plant at a speed of 1 m/sec is stopped, the zinc distribution on the band corresponds to the anode activity. In the practice, the power is shutdown for reasons of safety immediately after the band is stopped. In order to carry out the process all safety measures must be suspended. The process is very expensive and can be applied only exceptionally.

Hence, the present state-of-the-art does not offer any reasonable possibility to rapidly determine if a certain anode (or a segment thereof) requires reactivation or can continue to be in operation until the next intended standstill.

SUMMARY OF THE INVENTION

It is an object of the invention to visually inspect during a short-time standstill of an electrogalvanizing plant entire anodes in a test cell after a short-time interval which permits detecting a possible deactivation of areas of the activated layer.

The object is achieved inserting the anode to be tested between the cathode and anode of an electrolytic test call, applying a voltage therebetween, and visually inspecting the activated layer for the formation of gas bubbles. Absence of gas bubbles indicates the deactivated surface areas. A device for the working of the process has a trough-like electrolytic cell with a block-like interior; in this interior a pair of electrodes including anode and cathode is disposed on two opposing walls between which there is a holding device for the anode to be tested. Further, a lighting device is provided to inspect the active layer of the anode plate facing the cathode.

The gas bubbles which form if power is applied are recorded by means of a video camera in a window incorporated in the lateral wall of the trough.

It is particularly advantageous to inspect the activated layer of the anode without disassembling the latter into its individual segments, whereby the short-time interruption of the operation of a electrogalvanizing plant can be used for testing purposes. Using a chemically non-aggressive electrolyte such as a sodium sulfate solution results in easy and rapid handling.

DETAILED DESCRIPTION OF THE PREFERRED EMBODIMENTS

Figure 1:
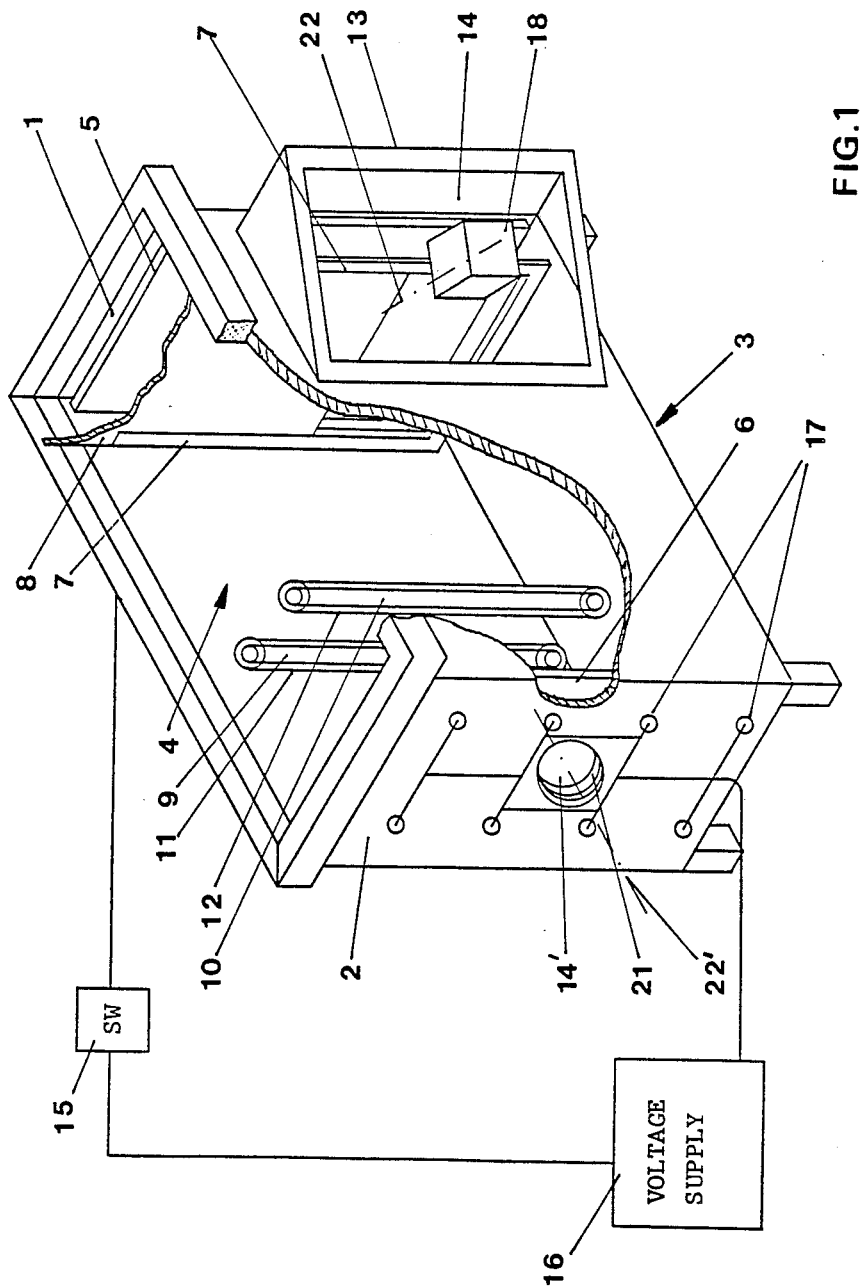
FIG. 1 is a cut-away perspective of an electrolytic cell.

According to FIG. 1, a flat rectangular anode 5 and a flat rectangular cathode 6 are disposed, respectively, at the opposing walls 1, 2 of an electrolytic cell 3 having a block-like interior 4. In the area of the anode 5 an electrically insulated holding device 7 having a U-shaped support profile is provided in which the anode 8 to be tested is downwardly introduced. The activated electrode surface is on the side facing toward the cathode 6. For reasons of clarity the anode 8 is only partially represented. Between the anode 8 and the fixed cathode 6 there is a lighting device including two longitudinally extended tube-like light sources 9, which, in turn, are surrounded by transparent protective tubes 11, 12, for example made of quartz glass. Compressed air is introduced between the light sources 9, 10 and the protective tubes in order to cool the lamps.

In the area of the holding device 7, the lateral wall of the trough 3 is provided with a laterally disposed prismatically shaped housing 13 which has a sealed inspection window 14 this window serves to inspect the anode in the holding device. The plane of the inspection window 14 includes together with the plane given by the holding device 7 of the anode to be tested an angle between 55° and 75°.

Via a switchgear 15, both, anode 5 and cathode 6 are connected to a constant voltage supply. The appertaining voltage supply points of the cathode bear the reference numerals 17. The arrangement corresponds to a bipolar electrochemical cell in which the rear side of the anode 8 (facing the anode 5) assumes the function of a cathode, whereas the front of the anode 8 (facing the cathode) is anodically operated. A diagrammatically represented video camera 18, the optical axis 22 of which is directed toward the anode 8 to be tested, is disposed in front of the inspection window 14.

Titanium is used as a material for the fixed electrodes 5, 6; the anode 8 to be tested can also be made of titanium. The fixed anode 5 as well as the anode 8 to tested are provided with an activated layer.

Polyvinyl chloride is preferably used as a material for the trough 3. The laterally disposed, prismatically shaped housing 13 is also made of PVC whereas compound glass is used for the inspection window. Sodium sulfate solution is preferably used as an electrolyte since this solution serves the safe and quick handling of the device due to its lack of chemical aggressiveness. During the test procedure bubbles of pure oxygen develop. It is also possible to use other electrolytes free from chloride ions such that the development of chlorine gas which includes risks is avoided It is furthermore possible to at least partially provide the wall 2 of the electrolytic cell adjacent to the cathode 6 with an inspection window 14' and provide a recess 21 in the cathode 6 through which the optical axis 22 of a video camera can be directed.

Figure 2:
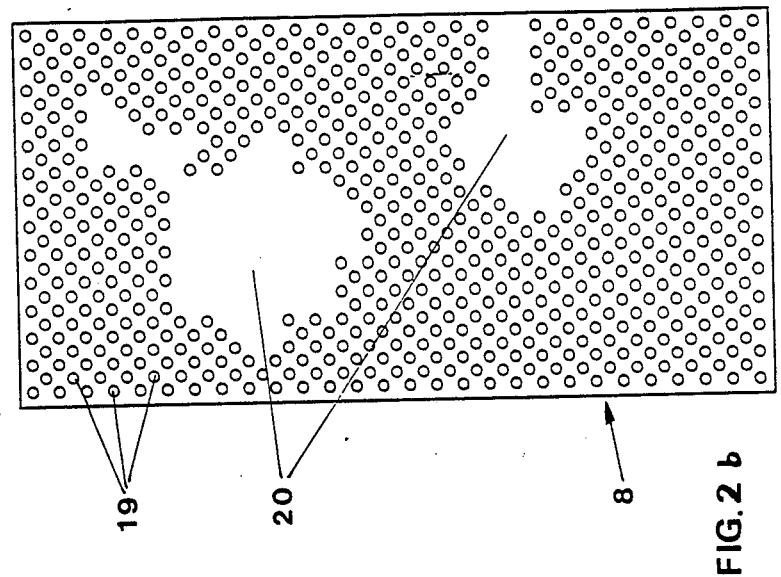
FIG. 2a is a diagrammatic view illustrating the development of gas bubbles on an activating layer of the electrode surface.
FIG. 2b is a diagrammatic view illustrating the development of gas bubbles on a deactivated area of the activating layer.
Figure 2:
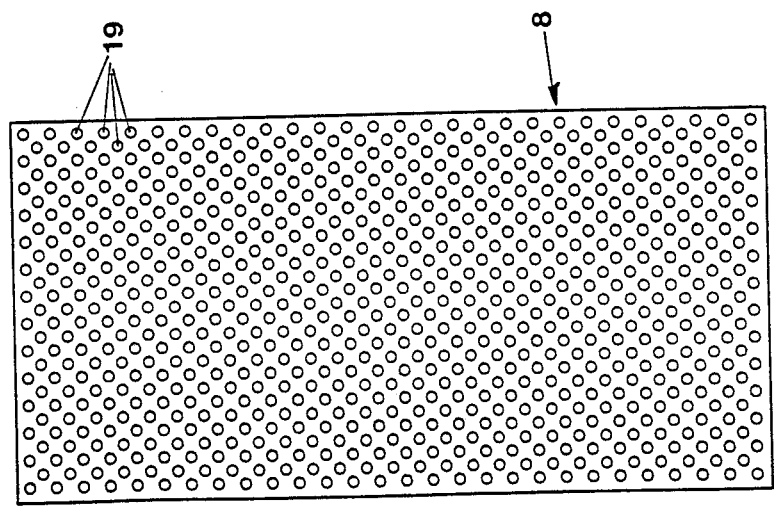

For inspecting, the electrolytic cell fitted with an anode plate 8 is connected to the constant Voltage supply 16 by rapid operation of the switchgear 15 (switch-on process: appr. 0.15 sec) such that an electric current flows in the electrolytic cell. At the same time, the light sources 9, 10 are switched on and the video camera is turned on to monitor the gas bubbles which form on the layer of the anode 8. This process typically covers a period of appr. 1 sec at a current density of 600 A/m$^2$. Only such a short-time current flow permits identifying deactivated areas of the activated layer; if the current passage times are longer, the deactivated areas can no more be identified since the entire activated layer is covered with gas bubbles. If the activated layer is fully functional, the gas bubbles are uniformly distributed over the entire anode surface, as it can be seen from FIG. 2a. If the anode surface has deactivated areas 20, these can be identified based on the missing gas bubbles according to FIG. 2b.

We claim:

1. Electrolytic test cell for identifying deactivated surface areas of an activated surface layer of a flat electrode for electrochemical processes, said cell comprising:
   an anode,
   a cathode,
   means for applying a voltage between said anode and said cathode,
   holding means for holding said electrode to be tested between said anode and said cathode so that said activated surface layer faces said cathode,
   a trough having transparent wall means to facilitate visually inspecting the activated surface layer of the electrode,
   means for illuminating the activated surface layer of the electrode, and
   a video camera directed toward the activated surface area.

* * * * *

UNITED STATES PATENT AND TRADEMARK OFFICE
CERTIFICATE OF CORRECTION

PATENT NO. : 4,963,244

DATED : October 16, 1990

INVENTOR(S) : Kotowski et al.

It is certified that error appears in the above-identified patent and that said Letters Patent is hereby corrected as shown below:

Column 2, line 56, after "sources 9," insert --10--.

Column 3, line 8, after "cathode" insert --6--.

Signed and Sealed this

First Day of September, 1992

Attest:

DOUGLAS B. COMER

*Attesting Officer*   Acting Commissioner of Patents and Trademarks